United States Patent
Kamei et al.

(10) Patent No.: US 6,590,122 B1
(45) Date of Patent: Jul. 8, 2003

(54) PROCESSES FOR PRODUCING POLYESTERS AND PRODUCING SORBIC ACID

(75) Inventors: Noboru Kamei, Himeji (JP); Akira Yamashita, Arai (JP); Mitsuhiro Kouno, Arai (JP)

(73) Assignee: Daicel Chemical Industries, Ltd., Osaka (JP)

( * ) Notice: Subject to any disclaimer, the term of this patent is extended or adjusted under 35 U.S.C. 154(b) by 0 days.

(21) Appl. No.: 09/555,228

(22) PCT Filed: Sep. 21, 1999

(86) PCT No.: PCT/JP99/05124

§ 371 (c)(1),
(2), (4) Date: May 26, 2000

(87) PCT Pub. No.: WO00/18819

PCT Pub. Date: Apr. 6, 2000

(30) Foreign Application Priority Data

Sep. 29, 1998 (JP) .......................................... 10-275657

(51) Int. Cl.⁷ .............................................. C07C 57/10
(52) U.S. Cl. ................. 562/601; 560/182; 560/210; 560/211
(58) Field of Search .................. 562/601; 560/210, 560/183, 211

(56) References Cited

U.S. PATENT DOCUMENTS 3,113,149 A  * 12/1963  Probst et al.
3,499,029 A  *  3/1970  Fernholz et al.
3,960,939 A  *  6/1976  Sekiyama et al.

FOREIGN PATENT DOCUMENTS

| JP | B455789 | 2/1970 |
| JP | B4536315 | 11/1970 |
| JP | B4730638 | 8/1972 |
| JP | B482528 | 1/1973 |
| JP | A62195341 | 8/1987 |
| JP | A291039 | 3/1990 |
| JP | A532853 | 2/1993 |
| JP | A9227447 | 9/1997 |
| JP | A1087795 | 4/1998 |
| JP | A1095745 | 4/1998 |

OTHER PUBLICATIONS

Derwent abstract (Acc. No. 1968–87264P) of DE 1244162 B (1968). Production of sorbic acid from crotonaldehyde and keten.*
Aldrich Handbook of Fine Chemicals and Laboratory Equipment, 2000–2001, p. 456.*

* cited by examiner

Primary Examiner—Paul J. Killos
(74) Attorney, Agent, or Firm—Birch, Stewart, Kolasch & Birch, LLP

(57) ABSTRACT

The invented process for producing a polyester supplies a crotonaldehyde with a purity of 95% by weight or more to a reaction system in the reaction of ketene with crotonaldehyde. In this process, unreacted crotonaldehyde may be recovered from a reaction mixture obtained by the reaction of ketene with crotonaldehyde and may be recycled to the reaction system. The αvinylcrotonaldehyde content of the crotonaldehyde to be supplied to the reaction system is, for example, less than 0.5% by weight, and the paraldehyde content of the crotonaldehyde to be supplied to the reaction system is, for example, less than 5% by weight. By decomposing the above-prepared polyester with, for example, hydrochloric acid, a sorbic acid having a satisfactory hue can be efficiently obtained.

3 Claims, No Drawings

PROCESSES FOR PRODUCING POLYESTERS AND PRODUCING SORBIC ACID

This application is the national phase under 35 U.S.C. § 371 of PCT International Application No. PCT/JP99/05124 which has an International filing date of Sep. 21, 1999, which designated the United States of America.

TECHNICAL FIELD

The present invention relates to a process for producing sorbic acid which is useful as food additives, and to a process for producing a polyester which is useful for the production of the sorbic acid.

BACKGROUND ART

As processes for the commercial production of sorbic acid, a process of reacting ketene with crotonaldehyde to yield a polyester and hydrolyzing the polyester in the presence of an acid or an alkali, and a process of decomposing the polyester by heat are known. For example, Japanese Examined Patent Application Publication No. 44-26646 discloses a process for producing sorbic acid. The process includes the steps of reacting ketene with crotonaldehyde in the presence of a catalyst to yield a reaction mixture, heating the reaction mixture under reduced pressure to remove unreacted crotonaldehyde and by-products of the reaction by distillation, thereby preparing a polyester containing the catalyst, decomposing the polyester with hydrochloric acid, and cooling the reaction mixture to yield sorbic acid.

A crude sorbic acid obtained by the decomposition of the polyester generally contains various colored substances and other impurities and is subjected to purification operations such as treatment with active carbon, distillation or recrystallization. The more the colored substances and other impurities are, the higher loads on the purification operation are and the more the loss of sorbic acid is.

Japanese Unexamined Patent Application Publication No. 54-163516 discloses a process of decomposing the polyester in the presence of a urea compound or the like to inhibit the formation of colored substances in the decomposition reaction of the polyester. Japanese Unexamined Patent Application Publication No. 9-227447 discloses a process of decomposing the polyester in stages and in a specific temperature range to obtain a sorbic acid which contains minimized tar content and is easily purified. However, these processes are not always commercially satisfactory, from the viewpoints of inhibitory effects of the by-production of colored substances and other impurities, the yield of sorbic acid, ease of operation, and costs.

DISCLOSURE OF INVENTION

Accordingly, an object of the invention is to provide a process for efficiently producing a sorbic acid having a satisfactory hue.

To achieve the above object, the present inventors made intensive investigations on a synthesis process of the polyester among a series of production processes of sorbic acid. As a result, they found that aldehydes and other impurities, especially high boiling impurities, contained in crotonaldehyde for use as a material of the synthesis of polyester decrease the yield of the polyester and deteriorate the hue and yield of the sorbic acid in the decomposition process of the polyester. This is probably because such impurities react with ketene. The inventors also found that the hue and yield of a crude sorbic acid obtained in the polyester decomposition process can be therefore markedly improved by setting the purity of crotonaldehyde to be supplied to a reaction system in the polyester decomposition process at a constant level or higher. The present invention has been accomplished based on these findings.

Specifically, the invention provides in an aspect a process for producing a polyester through a reaction of ketene with crotonaldehyde to yield a corresponding polyester. In the process, a crotonaldehyde with a purity of 95% by weight or more is supplied to a reaction system.

In another aspect, the invention provides a process for producing sorbic acid. This process includes the step of decomposing a polyester obtained by the aforementioned production process.

BEST MODE FOR CARRYING OUT THE INVENTION

According to the invention, ketene is reacted with crotonaldehyde to yield a polyester. The polyester is generally shown by the following formula (1):

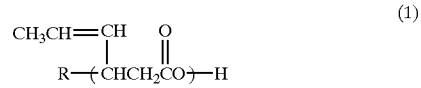

In the above formula, R is an acetoxy group or a hydroxyl group, and n denotes an integer of 2 or more (e.g., about 3 to 40).

The invention has a main feature in that a material crotonaldehyde to be supplied to the reaction system is to have a purity of 95% by weight or more in the polyester synthesis process, by which the polyester is prepared from ketene and crotonaldehyde. When unreacted crotonaldehyde is recovered from a reaction mixture derived from ketene and crotonaldehyde and the recovered crotonaldehyde is recycled to the reaction system, the purity of the overall crotonaldehyde to be supplied including the recovered crotonaldehyde and a crotonaldehyde newly supplied to the reaction system (hereinafter referred to as "fresh crotonaldehyde") is set at 95% by weight.

The purity of the material crotonaldehyde is preferably 97% by weight or more, more preferably 98% by weight or more, and particularly preferably 99% by weight or more.

As the fresh crotonaldehyde to be supplied to the reaction system, crotonaldehyde obtained by any production process can be used, such as crotonaldehyde obtained by the condensation of acetaldehyde, and crotonaldehyde obtained by allowing water to act on vinyl bromide in a concentrated sulfuric acid. For example, a commercially available high purity crotonaldehyde (e.g., crotonaldehyde with a purity of about 99.8% containing about 0.13% by weight of α-vinylcrotonaldehyde) can be advantageously employed. An industrially obtained crotonaldehyde generally contains various impurities according to its production process. Such impurities include, for example, acetaldehyde, α-vinylcrotonaldehyde, 2,4-hexadienal, and other aldehydes, 1,3-butadien-1-ol acetate, and acetone.

To improve the utilization ratio of the crotonaldehyde, crotonaldehyde should be preferably recovered from a reaction mixture derived from ketene and crotonaldehyde and be recycled to the reaction system. The recovered crotonaldehyde often contains, as impurities, paraldehyde which is by-produced in the reaction of ketene with crotonaldehyde, in addition to the α-vinylcrotonaldehyde.

The present inventors made detailed investigations on the relation of impurities contained in the crotonaldehyde to be supplied to the reaction system with the yield of the produced polyester and the hue and yield of the sorbic acid obtained by the decomposition of the polyester. They found that, of these impurities, α-vinylcrotonaldehyde, paraldehyde, and other aldehydes particularly decrease the yield of the polyester and deteriorate the hue and yield of the sorbic acid. The aldehydes are supposed to be converted into colored substances in the polyester synthesis process and/or polyester decomposition process.

In the polyester synthesis process, the overall crotonaldehyde to be supplied to the reaction system should have an α-vinylcrotonaldehyde content of preferably less than 0.5% by weight, and more preferably less than 0.45% by weight. The overall crotonaldehyde to be supplied to the reaction system should have a paraldehyde content of preferably less than 5% by weight, more preferably less than 2% by weight, and particularly less than 0.5% by weight.

When the fresh crotonaldehyde to be supplied to the reaction system has a purity of less than 95% by weight or when the recovered crotonaldehyde is recycled to the reaction system and the overall crotonaldehyde to be supplied to the reaction system has a purity less than 95% by weight, the crotonaldehyde can be purified by, for example, distillation and other purification means to a purity of 95% by weight or more prior to supplying to the reaction system. The purification by distillation can be performed by a step for removing low boiling impurities and/or a step for removing high boiling impurities. Particularly, the combination use of a step for removing low boiling impurities and a step for removing high boiling impurities is preferred. The purity and the impurity content of the crotonaldehyde can be controlled by appropriately selecting the theoretical plate number and the reflux ratio of a distillation column.

The reaction between ketene and crotonaldehyde is generally performed in the presence of a catalyst with or without an inert solvent.

Such catalysts include, but are not limited to, simple substances or compounds of manganese, cobalt, nickel, zinc, cadmium, and other transition metals; and pyridine, picoline, and other nitrogen-containing basic compounds. Examples of the compounds of the transition metals are oxides; salts of acetic acid, salts of isobutyric acid, salts of isovaleric acid, and salts of other organic acids; salts of sulfuric acid, salts of nitric acid, and salts of other inorganic acids; chlorides and other halides; acetylacetone complex salts, and other complex salts and complexes. Each of these catalysts can be used alone or in combination. The amount of the catalyst differs according to the type of the catalyst, but is generally about 0.1 to 10% by weight relative to the weight of ketene.

The supply ratio of the crotonaldehyde to ketene to the reaction system can be appropriately selected in consideration of, for example, reaction efficiency. The supply ratio by mole of the both (crotonaldehyde/ketene) is generally about 1 to 3, and preferably about 1.3 to 2.5.

A reaction temperature is, for example, about 20° C. to 100° C. and preferably about 25° C. to 80° C. The reaction can be performed in any of a continuous system, a semi-batch system, or a batch system.

A reaction mixture containing the polyester obtained by the reaction of ketene with crotonaldehyde is usually subjected to distillation to remove unreacted crotonaldehyde and low boiling impurities, and is then subjected to a decomposition reaction. Preferably, the unreacted crotonaldehyde removed by distillation is purified by, for example, distillation to a predetermined purity and is then recycled to the reaction system as described above.

The polyester may be decomposed by hydrolysis or by thermal decomposition, but is preferably decomposed by hydrolysis with a mineral acid, particularly with hydrochloric acid, for a higher yield. The polyester is hydrolyzed, for example, at temperatures ranging from about 10° C. to 110° C. When the polyester is hydrolyzed with hydrochloric acid, the concentration of hydrochloric acid is, for example, about 15 to 40% by weight. The polyester may be decomposed under atmospheric pressure, under reduced pressure, or under pressure.

Sorbic acid can be obtained by subjecting a mixture obtained by the decomposition of the polyester to a conventional separation and purification means. Such separation and purification means include crystallization, filtration, centrifugal separation, treatment with active carbon, distillation, and recrystallization.

The present invention can produce sorbic acid in a high yield and can markedly improve the coloring of a crude sorbic acid to mitigate loads on the purification process to thereby efficiently produce a purified sorbic acid. Especially, even when the recovered crotonaldehyde is recycled to the reaction system, a sorbic acid having a satisfactory hue can be efficiently obtained, and the invented process is greatly useful as an industrial production process.

The product sorbic acid and its salts can be used as preservatives for foods such as fish pastes, butters, cheeses, bean pastes, and jams.

The present invention supplies a high purity crotonaldehyde to the reaction system in the polyester synthesis process, and can produce a polyester in a high yield. In addition, a sorbic acid having a satisfactory hue can be efficiently obtained by the decomposition of the polyester. This is probably because the formation of substances adversely affecting the coloring is minimized.

The present invention will now be illustrated in further detail with reference to several inventive examples and comparative examples below, which are not intended to limit the scope of the invention. All "parts" are by weight unless otherwise specified.

EXAMPLE 1

To 600 parts of a crotonaldehyde with a purity of 99.3% by weight containing 0.15% by weight of α-vinylcrotonaldehyde and 0.1% by weight of paraldehyde, 2 parts of zinc isobutyrate was added as a catalyst, and 170 parts of a ketene gas was introduced at a temperature of 30° C. to 40° C. to perform a reaction. After the completion of reaction, excess crotonaldehyde was removed by distillation under reduced pressure to yield a highly viscous polyester. The yield of the polyester was 77% on the basis of ketene.

To 135 parts of the above-prepared polyester, 110 parts of a concentrated hydrochloric acid was added, and the resulting mixture was heated to 80° C. to decompose the polyester. The resulting mixture was separated by filtration, and was washed to yield 123 parts of a crude sorbic acid. A sodium hydroxide aqueous solution was added to the crude sorbic acid to yield a sodium sorbate aqueous solution, and to the solution 6 parts of active carbon was added, and the resulting mixture was stirred for 30 minutes. The mixture was filtrated to remove the active carbon, and a neutralization amount of a concentrated hydrochloric acid was added to the filtrate and the mixture was cooled to precipitate sorbic acid. The precipitated sorbic acid was separated by filtration, was washed, and was dried in vacuo to yield 114 parts of sorbic acid. The yield of sorbic acid was 84.7% on the basis of the polyester.

In 8.8 ml of a 1 N—NaOH aqueous solution, 1 g of the above-prepared sorbic acid was dissolved. The light transmittance of the solution at a wavelength of 400 nm was 80.9% as determined by a spectrophotometer using a 1-cm cell with a 1 N—NaOH aqueous solution as a reference.

EXAMPLE 2

A polyester was prepared in the same manner as in Example 1, except that a crotonaldehyde with a purity of 96.0% by weight containing 0.15% by weight of α-vinylcrotonaldehyde and 3.1% by weight of paraldehyde was used as a material. Sorbic acid was then prepared by decomposing the polyester with hydrochloric acid and treating the product with active carbon in the same manner as in Example 1. The obtained sorbic acid was dissolved in a 1 N—NaOH aqueous solution, and the light transmittance of the solution at 400 nm was determined. As a result, the yield of the polyester was 76.0% on the basis of ketene, the yield of sorbic acid was 84.1% on the basis of the polyester, and the light transmittance was 78.9%.

COMPARATIVE EXAMPLE 1

A polyester was prepared in the same manner as in Example 1, except that a crotonaldehyde with a purity of 90.0% by weight containing 0.15% by weight of α-vinylcrotonaldehyde and 9.4% by weight of paraldehyde was used as a material. Sorbic acid was then prepared by decomposing the polyester with hydrochloric acid and treating the product with active carbon in the same manner as in Example 1. The obtained sorbic acid was dissolved in a 1 N—NaOH aqueous solution, and the light transmittance of the solution at 400 nm was determined. As a result, the yield of the polyester was 70% on the basis of ketene, the yield of sorbic acid was 84.0% on the basis of the polyester, and the light transmittance was 61.0%.

COMPARATIVE EXAMPLE 2

A polyester was prepared in the same manner as in Example 1, except that a crotonaldehyde with a purity of 94.5% by weight containing 0.6% by weight of α-vinylcrotonaldehyde and 3.2% by weight of paraldehyde was used as a material. Sorbic acid was then prepared by decomposing the polyester with hydrochloric acid and treating the product with active carbon in the same manner as in Example 1. The obtained sorbic acid was dissolved in a 1 N—NaOH aqueous solution, and the light transmittance of the solution at 400 nm was determined. As a result, the yield of the polyester was 72.5% on the basis of ketene, the yield of sorbic acid was 82.5% on the basis of the polyester, and the light transmittance was 63.0%.

What is claimed is:

1. A process for producing sorbic acid having a light transmittance, in a solution in which 1 gram of the sorbic acid is dissolved in 8.8 milliliters of a 1 Normal NaOH aqueous solution at a wavelength of 400 nm, of approximately 80% or more, said process comprising the steps of:

recovering unreacted crotonaldehyde from a reaction mixture formed by reacting ketene with crotonaldehyde in a reaction system and recycling the recovered crotonaldehyde to the reaction system, providing a mixture consisting essentially of
(a) crotonaldehyde, inclusive of said recovered crotonaldehyde, having a purity of at least 95% by weight, and α-vinylcrotonaldehyde content of less than 0.5% by weight, and a paraldehyde content of less than 5% by weight and
(b) a catalyst comprising a compound selected from the group consisting of transition metal salts and oxides, introducing (c) ketene into said reaction mixture to yield a corresponding polyester, and decomposing the polyester so obtained with a strong mineral acid to yield sorbic acid having a light transmittance, in a solution in which 1 gram of the sorbic acid is dissolved in 8.8 milliliters of a 1 Normal NaOH aqueous solution at a wavelength of 400 nm, of approximately 80% or more.

2. The process for producing sorbic acid according to claim 1, wherein said polyester is decomposed in the presence of hydrochloric acid.

3. A process for producing a polyester by reacting ketone with crotonaldehyde, said process comprising the steps of:

providing crotonaldehyde to a reaction system, distilling the crotonaldehyde to remove low boiling impurities therefrom, distilling the crotonaldehyde to remove high boiling impurities therefrom, reacting ketene with said crotonaldehyde having a purity of 95% by weight or more to yield a reaction mixture, recovering unreacted crotonaldehyde from said reaction mixture, and recycling the recovered crotonaldehyde to the reaction system.

* * * * *